US006806400B1

(12) United States Patent
Pruss et al.

(10) Patent No.: US 6,806,400 B1
(45) Date of Patent: Oct. 19, 2004

(54) METHOD FOR ENHANCING PATHOGEN RESISTANCE IN PLANTS

(75) Inventors: Gail J. Pruss, Columbia, SC (US); Vicki B. Vance, Columbia, SC (US)

(73) Assignee: University of South Carolina, Columbia, SC (US)

( * ) Notice: Subject to any disclaimer, the term of this patent is extended or adjusted under 35 U.S.C. 154(b) by 113 days.

(21) Appl. No.: 09/711,380

(22) Filed: Nov. 9, 2000

Related U.S. Application Data

(60) Provisional application No. 60/165,392, filed on Nov. 12, 1999.

(51) Int. Cl.[7] ........................ C12N 15/82; C12N 15/90; A01H 1/00
(52) U.S. Cl. ...................................... 800/280; 800/265
(58) Field of Search ............................... 435/410, 419, 435/468; 800/278–280, 295, 298, 301, 260, 265

(56) References Cited

U.S. PATENT DOCUMENTS

| 5,576,202 A | 11/1996 | Pehu et al. ................. 435/468 |
| 5,939,541 A | 8/1999 | Vance et al. ................ 536/24.1 |
| 5,968,828 A | 10/1999 | Pehy et al. ................. 435/418 |
| 6,207,882 B1 * | 3/2001 | Ding .......................... 800/301 |
| 6,395,962 B1 * | 5/2002 | Vance ......................... 800/278 |

FOREIGN PATENT DOCUMENTS

| WO | 9951749 | 10/1999 | ........... C12N/15/40 |
| WO | 9958696 | 11/1999 | ........... C12N/15/82 |

OTHER PUBLICATIONS

Lucy et al., EMBO J., 2000, vol. 19, pp. 1672–1680.*
Dunoyer et al., Plant J., 2002, vol. 29, pp. 555–567.*
Mirkov et al., Phytopathology, vol. 91, p. S161.*
Hong–Wei Li et al., "Strong host resistance targeted against a viral suppressor of the plant gene silencing defence mechanism," *The EMBO Journal*, vol. 18, No. 10, pp. 2683–2691.
Shi, et al., "Mutations in the Region encoding the Central Domain of Helper Component–Proteinase (HC–Pro) Eliminate Potato Virus X/Potyviral Synergism," *Virology* 231, 35–42 (1997).
Revers et al., New Advances in Understanding the Molecular Biology of Plant/Potyvirus Interactions, Molecular Plant–Microbe Interactions, vol. 12, No. 5, 1999, 367–376.
Sonoda, Shoji et al., "Resistance against a heterologous Potyvirus in Transgenic Tobacco Plants Expressing Antisense RNA of HC–Pro Gene of Sweet Potato Feathery Mottle Potyvirus," *Annals of Phytopathol. Soc. Jpn.* 64: 183–186 (1998).

Ward et al., "Coordinate Gene Activity in Response to Agents that Induce Systemic Acquired Resistance." ,*The Plant Cell* 3: 1085–1094, 1991.
Dong, Xinnian "SA, JA, Ethylene, and Disease Resistance in Plants, " *Current Opinion in Plant Biology* 1:316–323, 1998.
Chen et al., "Induction, Modification, and Transduction of the Salicyclic Acid Signal in Plant Defense Response,"*Proc. Natl. Acad. Sci.* USA 92: 4134–4137, 1995.
Hunt and Ryals, "Systemic Acquired Resistance Signal Transduction," *Crit. Rev. Plant Sci.* 15:583–606, 1996.
Neuenschwander et al., "Systemic Acquired Resistance," pp. 81–106 in *Plant–Microbe Interactions*, vol. 1, Chapman and Hall, New York, 1996.
Shirasu et al., "Signal Transduction in Plant Immunity," *Curr. Opin Immunol.* 8: in press, 1996.
Metraux et al., "Induced Resistance in Cucumber in Response to 2,6–Dichloroisonicotinic Acid and Pathogens," pp. 432–439 in *Advances in Molecular Genetics of Plant–Microbe Interactions*, Kluwer Academic Publishers, the Netherlands, 1991.
Ryals et al., "Systemic Acquired Resistance," *The Plant Cell* 8: 1809–1819, 1996.
P. Reymond and E. E. Farmer, "Jasmonate and Salicylate as Global Signals for Defense Gene Expression," *Current Opinion in Plant Biology*, 1:404–411, 1998.
Vance et al., "5 'Proximal Potyviral Sequences Mediate Potato Virus X/Potyviral Synergistic Disease in Transgenic Tobacco," *Virology*206, 583–590, 1995.
Brignetti et al., *EMBO J.* 17, 6739–6746, 1998.
Beclin et al., *Virology* 252, 313–317.
Voinnet, O. et al. *Proc. Natl. Acad. Sci USA* 96, 14147–14152, 1999.

* cited by examiner

*Primary Examiner*—Ashwin Mehta
(74) *Attorney, Agent, or Firm*—Alston & Bird LLP

(57) ABSTRACT

The present invention provides a method for inducing or enhancing resistance in plants by supplying to the plant a virally encoded booster sequence comprising the 5' proximal region of the potyvirus genome or by supplying other sequences encoding suppressors of gene silencing alone or in combination. Supplying the booster sequence to a plant, by means of stable transformation into the genome of the plant or introduced by expression from a plant viral expression vector, induces or enhances resistance in a plant against a broad range of pathogens, including viral, fungal and bacterial infectious agents.

12 Claims, 11 Drawing Sheets

Blue Mold Infections

Constitutive Expression of HC-Pro Confers High-level Resistance to Blue Mold Disease

Peronospora tabacina Spore Production # of spores x 10³/cm² leaf area

Vector Control: ~580

U6B: ~80

METHOD FOR ENHANCING PATHOGEN RESISTANCE IN PLANTS

CROSS-REFERENCE TO RELATED APPLICATION

This application claims the benefit of U.S. Provisional Application No. 60/165,392, filed Nov. 12, 1999, which is hereby incorporated herein in its entirety by reference.

The present invention is directed to the field of inducing resistance in plants to a broad range of pathogens. Specifically, the invention relates to methods of inducing resistance in plants against a variety of viruses, bacteria, and fungal pathogens by expression of a viral polyprotein encoded by members of the potyvirus group of plant viruses or by expression of other suppressors of gene silencing.

BACKGROUND OF THE INVENTION

The survival of a plant attacked by an invading pathogen depends upon a number of factors. One important factor is how quickly the plant responds and mounts a defense to the pathogen, including the induction of both local and systemic pathways for resistance. Local responses to pathogen attack include callose deposition, physical thickening of cell walls (lignification), synthesis of compounds which exhibit antibiotic activity (e.g., phytoalexins), and the production of protein molecules like cell wall hydrolases (Ward et al., "Coordinate Gene Activity in Response to Agents that Induce Systemic Acquired Resistance," *The Plant Cell* 3: 1085–1094, 1991; the contents of which is incorporated herein in its entirety).

In addition to mounting a local response, plants may also employ general resistance mechanisms to prevent an infection from spreading or to fight secondary infections from a broad array of pathogens. For example, induction of a hypersensitive response (HR), resulting from the interaction of a specific resistance gene from the plant with the corresponding avirulence gene from the pathogen, results in localized cell death and permits a plant to mount a rapid defense against a pathogenic organism (Dong, Xinnian, "SA, JA, Ethylene, and Disease Resistance in Plants," *Current Opinion in Plant Biology* 1: 316–323, 1998; the contents of which is incorporated herein in its entirety).

Another general mechanism of resistance, which may be induced either after an HR response or during an active infection, is known as systemic acquired resistance (SAR). SAR refers to a distinct signal transduction pathway which results in the development of a broad-spectrum resistance (for a general review of the SAR pathway, see Chen et al., "Induction, Modification, and Transduction of the Salicyclic Acid Signal in Plant Defense Responses," *Proc. Natl. Acad. Sci.* USA 92: 4134–4137, 1995; Hunt and Ryals, "Systemic Acquired Resistance Signal Transduction," *Crit. Rev. Plant Sci.* 15: 583–606, 1996; Neuenschwander et al., "Systemic Acquired Resistance," pgs. 81–106 in *Plant-Microbe Interactions*, Vol. 1, Chapman and Hall, New York, 1996; and Shirasu et al., "Signal Transduction in Plant Immunity," *Curr. Opin. Immunol.* 8: in press, 1996; the contents of which are incorporated herein in their entirety).

The accumulation of salicylic acid (SA) in plants is believed to serve as one signal for the onset of SAR, since the removal of SA in transgenic plants expressing salicylate hydroxylase prevents SAR from being established (Dong, 1998). In some plants, studies have demonstrated that SA alone is sufficient for SAR induction. For example, treatment of plants such as tobacco, cucumber, and Arabidopsis with SA, or its functional analogues, induces SAR (Metraux el al., "Induced Resistance in Cucumber in Response to 2,6-Dichloroisonicotinic Acid and Pathogens," pgs. 432–439 in *Advances in Molecular Genetics of Plant-Microbe Interactions,* Kluwer Academic Publishers, The Netherlands, 1991; the contents of which is incorporated herein in its entirety.)

Tobacco remains one of the best characterized models of SAR. In tobacco, SAR has been shown to provide resistance against seven of nine tobacco pathogens, including infection with fungal, bacterial, and viral isolates (Ryals et al., "Systemic Acquired Resistance," *The Plant Cell* 8:1809–1819, 1996; the contents of which is incorporated herein in its entirety).

SAR is not the only mechanism used by plants to induce a broad-spectrum resistance. Evidence indicates that other signals may play a role in the induction of resistance against microbial pathogens. For example, two alternative signal molecules, jasmonic acid and ethylene, have been shown to induce resistance, as well as mediate the wounding response in plants (Dong, 1998).

In addition to signal molecules which induce resistance pathways, it is known that plants contain many genes which encode for defense-related proteins. In addition to the genes involved in mediating HR, and encoding signal transduction molecules like SA, genes encoding pathogenesis-related (PR) proteins, such as phytoalexins, and enzymes involved in providing stress protection and repairing tissue damage are important mediators of protection in plants (P. Reymond and E. E. Farmer, "Jasmonate and Salicylate as Global Signals for Defense Gene Expression," *Current Opinion in Plant Biology,* 1: 404–411, 1998; the contents of which is incorporated herein in its entirety).

Although it was previously known that exposure to certain pathogens could induce both local protective responses as well as elicit a state of general resistance to a broad range of plant pathogens, the present invention represents the first example of inducing such general resistance by ectopic expression of a viral polyprotein encoded by members of the potyvirus group of plant viruses. The nucleotide sequence encoding this polyprotein, and responsible for the induction of this generalized resistance in plants, has been identified as the P1/HC-Pro sequence.

Previously, the present inventors demonstrated that the potyvirus P1/HC-Pro sequence could function to suppress post-transcriptional gene silencing in plants, thus providing a method to enhance the expression of either foreign or endogenous genes introduced into plants transformed with this "booster" sequence (U.S. Pat. No. 5,939,541 to Vance et al., the contents of which is incorporated herein in its entirety).

For purposes of this specification, the term "booster sequence" refers to the P1/HC-Pro sequence of a potyvirus, or at least the part of the P1/HC-Pro coding sequence able to induce a generalized resistance in plants transformed with that sequence.

The term "gene" or "genes" is used to mean nucleic acid sequences (including both RNA or DNA) that encode genetic information for the synthesis of a whole RNA, a whole protein, or any functional portion of such whole RNA or whole protein sufficient to possess a desired characteristic. Genes that are not part of a particular plant's genome are referred to as "foreign genes" and genes that are a part of a particular plant's genome are referred to as "endogenous genes." The term "gene products" refers to RNAs or proteins that are encoded by the gene. "Foreign gene products" are RNA or proteins encoded by foreign genes and "endogenous gene products" are RNA or proteins encoded by endogenous genes.

The initial step in the present discovery of the viral booster sequence was the finding that PVX/potyviral synergistic disease syndrome, characterized by increases in symptom severity and in accumulation of the PVX pathogen, does not require infection with both viruses. This was reported by Vance, et al. in "5' Proximal Potyviral Sequences Mediate Potato Virus X/Potyviral Synergistic Disease in Transgenic Tobacco." 206 *Virology*, 583–590 (1995). The synergistic disease is mimicked in plants expressing only a subset of the potyviral genomic RNA and infected singly with PVX. The potyviral region shown to mediate the synergistic disease comprises the 5'-proximal 2780 nucleotides of the genomic RNA, including the 5'-untranslated region (5'-UTR) and the region encoding the potyviral gene products P1, helper component-proteinase (HC-Pro), and a portion of P3. This described potyviral region is referred to herein as the "P1/HC-Pro sequence."

Thus, Vance et al. (1995), identified a disease determinant carried by the potyvirus genome (the P1/HC-Pro sequence), and this disease determinant was shown to mediate the well-known PVX/potyviral synergistic disease. Although the mechanism by which this potyviral sequence mediated the PVX/potyviral synergistic disease was unknown, it was postulated to involve a specific, direct interaction of the potyviral P1/HC-Pro RNA sequence or the encoded potyviral gene products with the genomic RNA or replication proteins of the interacting PVX pathogen. Although the potyviral P1/HC-Pro sequence was found to boost accumulation of the PVX viral structural gene (coat protein) and the accumulation of the PVX viral particle, this enhanced accumulation was thought to be specific for the native PVX genes expressed from the native PVX genome. Furthermore, the enhanced accumulation of PVX coat protein and PVX virus particles was tightly correlated with the perceived detrimental and undesirable increase in disease symptoms.

Accordingly, it would be beneficial if methods of inducing generalized resistance in plants could be developed, especially if the induction of such resistance did not require initial infection with a pathogen. Additionally, it would be especially beneficial if the induced resistance functioned to protect the plant from a broad spectrum of pathogens, including infection by viral, bacterial, and fungal organisms. The present invention overcomes some of the deficiencies of prior methods to elicit general resistance in plants by using a particular boosting sequence obtained from a potyvirus or by using other sequences encoding suppressors of gene silencing, particularly suppressors of PTGS (such as, for example, the CMV suppressor of PTGS [Brignetti et al;, *EMBO J.* 17, 6739–6746, 1998; Beclin et al., *Virology* 252, 313–317, 1998]). Other suppressors which are useful according to the teachings herein are known to those skilled in the art and can be found, for example, in Voinnet, O., et al., *Proc. Natl. Acad. Sci. USA* 96, 14147–14152, 1999.

SUMMARY OF THE INVENTION

It is an object of the present invention to provide methods for enhancing resistance in plants.

Another object of the present invention is to provide methods of enhancing resistance in plants against a broad spectrum of pathogenic organisms.

A further object of the present invention is to provide processes using a particular booster sequence to induce general resistance against infection in a plant.

Yet a further object of the invention is to provide a method of inducing or enhancing resistance in a plant by providing a virally encoded or other suppressor(s) of gene silencing.

These and other objects are achieved by providing a method for inducing resistance in plants by supplying a virally encoded booster sequence comprising the 5' proximal region of the potyvirus genome, which may preferably include the coding region for P1, helper component-proteinase (HC-Pro), and a small portion of P3. Alternatively, some portion of the booster sequence sufficient to induce resistance may be expressed either individually or fused to other sequences. Additionally, a modified version of the booster sequence, a related sequence from another virus, or any portion or modified version of that related sequence expressed either individually or fused to another sequence can be employed. It is well known in the art to generate fragments or otherwise modified versions of known sequences by, for example, use of such compounds or methods as Bal 31 exonuclease, restriction enzymes, point mutations, or polynucleotide synthesis. The function of such fragments or modified versions can easily be verified by following the steps taught herein and as specifically exemplified below. Such functional fragments or modifications are included within the scope of the term "booster sequence." The booster sequence induces resistance against a broad spectrum of pathogenic organisms when suppressed in plants, including viral, bacterial, and fungal organisms.

The process of inducing resistance in plants may be carried out by various methods. For example, the booster sequence may be provided to the plant in a variety of ways. It may be provided by infection with a virus that expresses the booster sequence as a native viral gene product during its natural life cycle. Alternatively, the booster sequence may be introduced through use of a transgenic host plant expressing the booster sequence as an introduced gene. The booster sequence may also be introduced using the same viral expression vector utilized to introduce foreign or endogenous genes of interest. A transient expression system may also be employed to temporarily express the booster sequence.

More specifically, the present invention involves a method of inducing or potentiating resistance in a plant by supplying a virally encoded booster sequence comprising the 5' proximal region of the potyvirus genome, which preferably includes the coding region for P1, helper component-proteinase (HC-Pro), and a small portion of P3. The booster sequence is introduced into plant material, which includes plant cells, plant protoplasts, or whole plants, so that resistance of the plant to a broad range of pathogens is induced or potentiated, even before the plant containing the booster sequence has come into contact with the pathogen. The 5' proximal region supplied may comprise the coding region for P1, helper component-proteinase (HC-Pro) and a small portion of P3. The portion of the 5' proximal region may be expressed independently or fused to other sequences.

Transformation of the plant material with the potyvirus booster sequence, comprising the 5' proximal region, induces or potentiates general resistance pathways in the plant. The induced or potentiated resistance is to a broad range of pathogens, including viral, bacterial, and fungal isolates. For example, in one embodiment, transgenic plants expressing the booster sequence exhibit enhanced resistance to Tobacco Mosaic Virus (TMV). In a similar fashion, plants supplied with the booster sequence also exhibit increased resistance to fungal infections (i.e., blue mold infection, caused by the pathogen Peronospora tacacina).

The booster sequence may be supplied in a number of ways and by various methods well known to those skilled in the art. For example, the booster sequence may be supplied to a plant (or plant material) by co-infection with a potyvirus that expresses the native booster sequence encoded by that potyvirus; introduction via a viral expression vector with the booster sequence being supplied by co-infection with a potyvirus that expresses a nonnative version of said booster sequence; or introduction via a viral expression vector having the gene fused to the structural gene of said viral expression vector.

Alternatively, the booster sequence may be supplied via expression from one or more DNA copies of the booster sequence stably incorporated into the plant genome prior to, during, or after transformation of the plant material with said introduced gene product according to methods well known to those skilled in the art.

In yet another embodiment according to the present invention, the booster sequence may be operatively linked to an expression control sequence to optimize expression. Recombinant DNA in accordance with the present invention may be in the form of a vector (for example, a plasmid, cosmid, or phage). The vector may be an expression vector, having various regulatory sequences to drive expression, or a cloning vector not having regulatory sequences.

As one of skill in the art of molecular biology will recognize, the booster sequence may be supplied in a number of ways to a host plant. Various teachings may be consulted to determine how to make transgenic plants containing the booster sequence, without undue experimentation. In particular, the following references may be consulted; the contents of which are hereby incorporated by reference in their entirety; Sambrook et al., *Molecular Cloning: A Laboratory Manual,* Cold Spring Harbor Laboratory, Cold Spring Harbor Press, New York, 1989; Ausubel et al., *Current Protocols in Molecular Biology,* John Wiley & Sons, New York, 1989; and Gee et al. in Huber and Carr, "Molecular and Immunologic Approaches," Futura Publishing Co., New York, 1994.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying figures as follows:

FIGS. 1A, 1B, and FIG. 1C show TMV-inoculated leaves of U6B and vector control at Day 6 post-inoculation, at Day 5 post-inoculation, and at Day 7 inoculation, respectively.

FIG. 5. Mild symptoms of blue mold infection on transgenic line U-6B compared to severe symptoms on the control. The figure on the left shows wilting symptoms: severe in vector, absent in U6B. The figure on the right shows spore production on leaves removed from infected plants and put in sporulation conditions. The vector leaf is entirely covered with spores, and the U6B leaf isolated patches of spores.

FIG. 6. Reduced spore production in transgenic line U-6B compared to the control when infected with blue mold.

FIG. 8A and FIG. 8D show trypan blue staining for fungal hyphae in a *Peronospora tabacina*-infected leaf of Vector and U6B, respectively.

DETAILED DESCRIPTION OF THE PREFERRED EMBODIMENT

Figure 1:
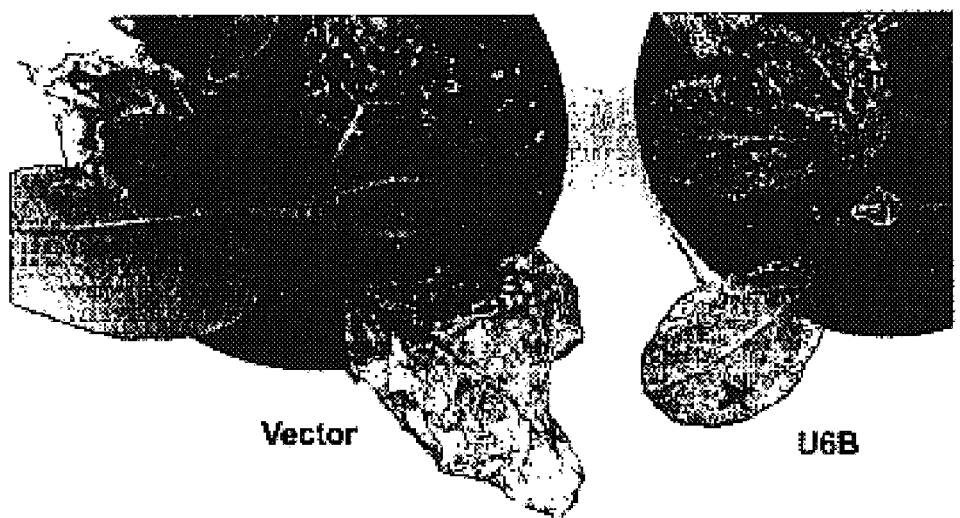
FIG. 1. Local lesions of TMV infection on inoculated leaves of P1/HC-Pro transgenic and control plants showing the reduced size of lesions of P1/HC-Pro transgenic plants.
Figure 1:
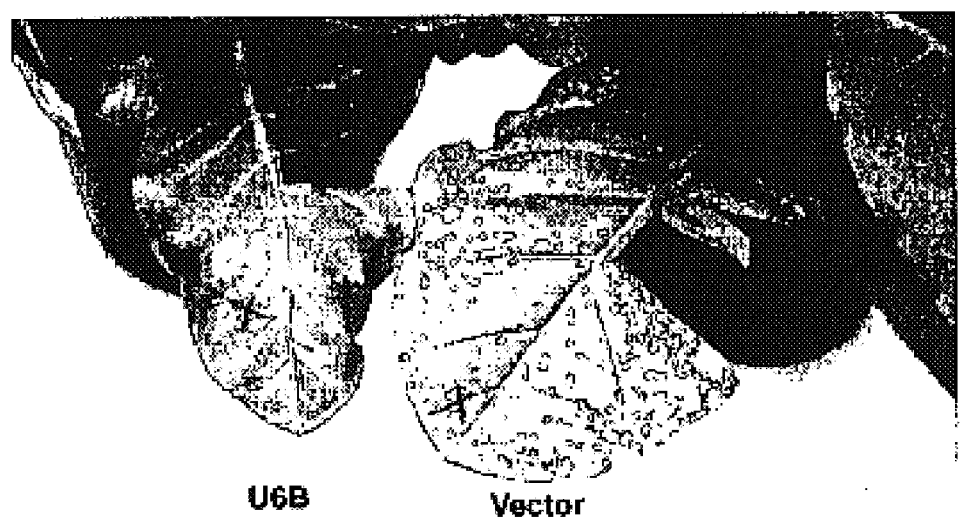

Other objects, features, and aspects of the present invention are discussed in greater detail below. It is to be understood by one of ordinary skill in the art that the present discussion is a description of exemplary embodiments only and is not intended as limiting the broader aspects of the present invention, which broader aspects are embodied in the exemplary construction.

The present invention employs a virally encoded booster sequence comprising the 5' proximal region of the potyvirus genome, or some portion of or modified form thereof, supplied to a plant in a method for inducing or potentiating general resistance against a broad range of pathogens. The booster sequence induces or potentiates one or more of a plant's resistance pathways such that the plant is resistant against a broad spectrum of infectious agents, including viral, fungal, and bacterial pathogens.

Contrary to previous beliefs, the potyviral P1/HC-Pro sequence is not merely the specific disease determinant for PVX/potyviral synergism. Instead, the potyviral P1/HC-Pro sequence functions in a general fashion, enhancing resistanceagainst a broad spectrum of pathogenic agents.

The P1/HC-Pro sequence not only enhances the expression of a native viral gene from its native viral genomes, as shown by Vance et al. ("5' Proximal Potyviral Sequences Mediate Potato Virus X/Potyviral Synergistic Disease in Transgenic Tobacco," *Virology* 206: 583–590, 1995) and the expression of PVX coat protein, but also enhances the expression of foreign genes contained in a plant viral expression vector (Vance et al. In U.S. Pat. No. 5,939,541).

It is known that the boosting action of the P1/HC-Pro sequence may be separated from its detrimental effects on the plant. Experiments using genetically modified or fused versions of the potyviral P1/HC-Pro sequence have identified regions that are required to induce or enhance and regions that are required for the detrimental disease promoting action of the sequence. Although the two identified regions overlap, it is possible to modify the sequence such that the induction of resistance occurs without causing detrimental disease symptoms. Thus, the invention provides a method to induce or enhance resistance in plants in the absence of detrimental effects on the host plant when such disease symptoms are deemed undesirable for the intended purpose.

EXAMPLE 1

Enhanced Resistance to a Broad Range of Pathogens Conferred by the Potyviral P1/HC-Pro Booster Transgenic tabacco plants (Nicotiana tabacum) expressing the P1/HC-Pro sequence [transgenic lines U-6B, TEV C, and TEV 1] are described in Carrington, J. D., Freed, D. D. and Oh, C-S, "Expression of Potyviral Polyproteins in Transgenic Plants Reveals Three Proteolytic Activities Required for Complete Processing," 9 *EMBO J.*, 1347–1353 (1990); Vance V. B. Berger, P. H., Carrington, J. C., Hunt, A. G., and Shi X. M., in "5' Proximal Potyviral Sequences Mediate Potato Virus X/Potyviral Synergistic Disease in Transgenic Tobacco," 206 *Virology*, 583–590 (1995); and Shi et al, "Mutations in the Region Encoding the Central Domain of Helper Component-Proteinase (HC-Pro) Eliminate Potato Virus X/Potyviral Synergism," Virology 231: 35–42, 1997;] the contents of which are herein incorporated by reference in their entirety. Control tobacco plants of the same line did not express this sequence.

The methods used for growing control and transgenic plants, virus inoculation, and sampling were described previously in Vance, Vicki, "Replication of Potato Virus X RNA is Altered in Coinfections with Potato Virus Y," *Virology* 182: 486–494, 1991; Vance et al., in "5' Proximal Potyviral Sequences Mediate Potato Virus X/Potyviral Synergistic Disease in Transgenic Tobacco," 206 *Virology*, 583–590 (1995); Shi et al., "Mutations in the Region Encoding the Central Domain of Helper Component-Proteinase (HC-Pro) Eliminate Potato Virus X/Potyviral Synergism," *Virology* 231: 35–42, 1997; and Pruss et al., "Plant Viral Synergism: The Potyviral Genome Encodes a Broad-Range Pathogenicity Enhancer that Transactivates Replication of Heterologous Viruses," *The Plant Cell* 9: 859–868, 1997; the contents of which are incorporated by reference herein in their entirety.

The virus isolates used in these experiments included tobacco mosaic virus (TMV) and the Scottish serotype strain W22 of tomato black ring virus (TBRV (s) W22, accession number D00322, Greif et al., *Journal of General Virology* 69: 1517–1529, 1988), provided from Dr. David Baulcombe (Sainsbury Laboratory, Norwich, UK). For most experiments, virus stocks consisted of sap from infected leaves of *N. clevelandii*.

Inoculation and sampling procedures used were as described previously (Pruss et al., 1997). Briefly, one or more lower leaves from developmentally matched sets of transgenic and control plants were mechanically inoculated with virus. At the indicated times after inoculation, representative sections of leaves (excluding the midvein) were excised with razor blades for immediate isolation of total RNA or protein. In the experiment shown in FIG. 1C and FIG. 3C, entire inoculated leaves were excised. Excised sections were immediately frozen at −70° C., and later ground in liquid nitrogen.

RNA was isolated as described previously (Pruss et al., 1997). Total RNA isolated from leaves of infected plants was analyzed using Northern blots. A radioactive probe complementary to the entire TMV (+) strand RNA was generated using reverse transcriptase, hexanucletoide random primers, and TMV genomic RNA isolated from purified virus. A probe complementary to TBRV RNA 1 was prepared using a DNA labelling kit with a PCR-generated cDNA fragment of about 1000 bp of TBRV RNA 1 as template. Quantitation of the levels of viral RNA was performed using a phosphorimager.

Protein isolated from leaves of TMV-infected plants was analyzed using Western blots. Antiserum specific to TMV coat protein was used as primary antiserum, and immunoreactive proteins were visualized using a goat anti-rabbit antiserum conjugated to alkaline phospliatase.

Figure 1C:
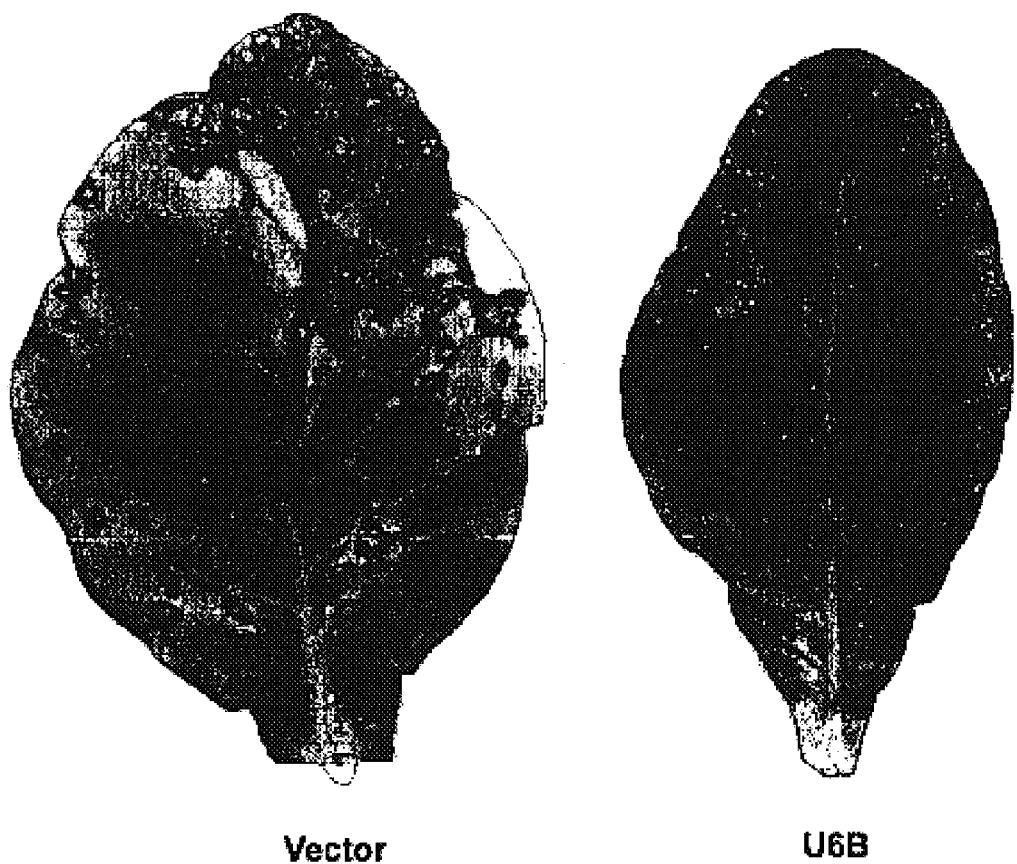
Figure 2:
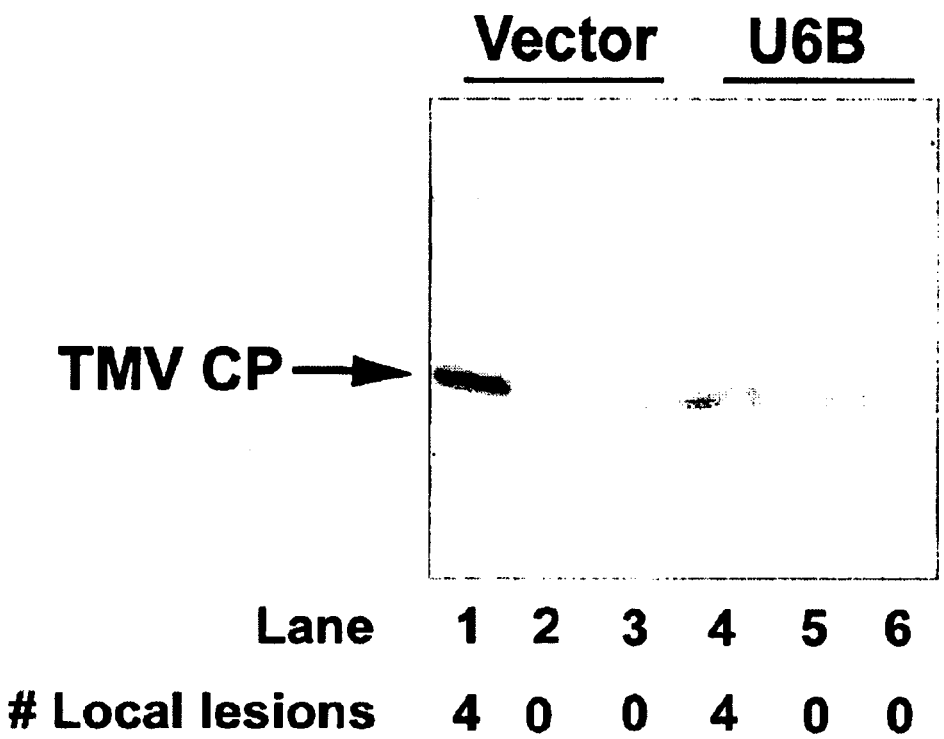
FIG. 2. Western blot showing the reduced level of TMV coat protein in P1/HC-Pro transgenic line U-6B compared to the control when infected with TMV.
Figure 3:
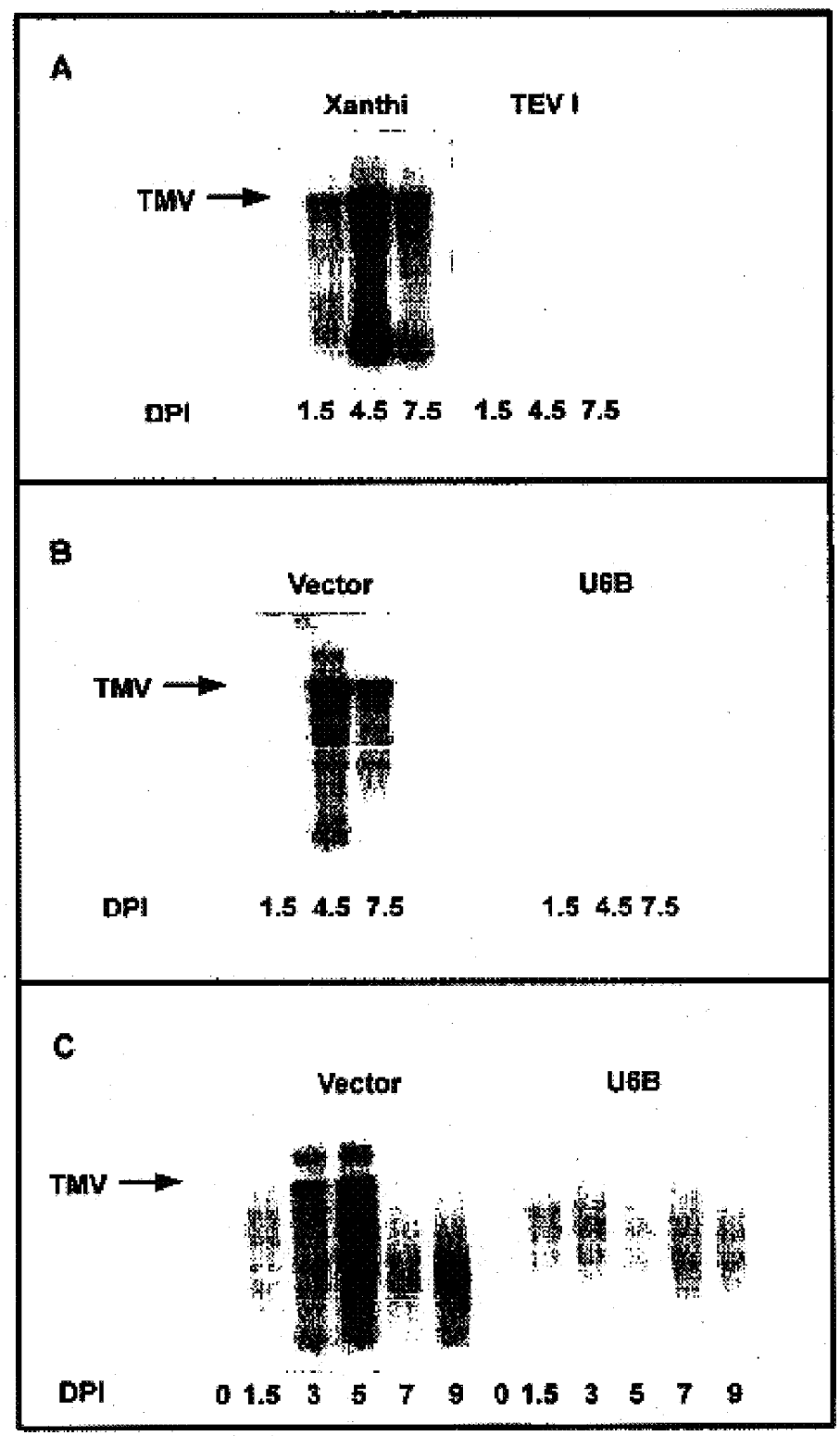
FIG. 3. Panels A, B, and C are northern blots showing the reduced level of TMV genomic RNA in P1/HC-Pro transgenic lines U-6B and TEV 1 compared to the controls when infected with TMV. Panel D shows the absence of local lesions on TMV-inoculated leaves of P1/HC-Pro transgenic line TEV 1.
Figure 3D:
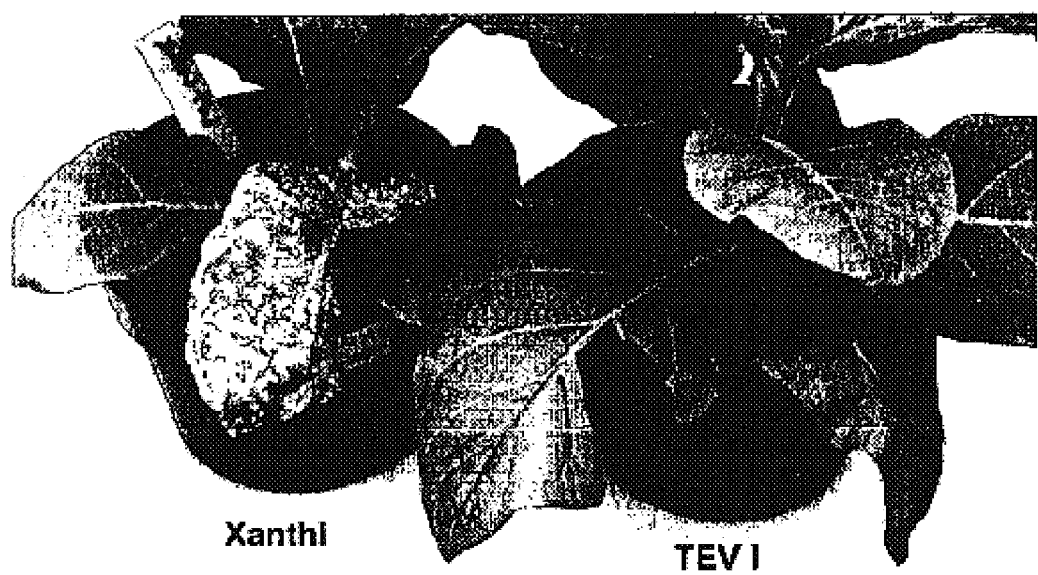
Figure 4:
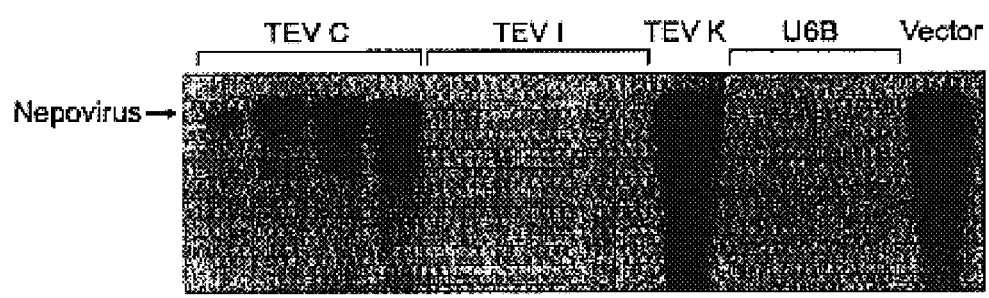
FIG. 4. Northern blot showing the reduced level of TBRV RNA 1 in P1/HC-Pro transgenic lines U-6B, TEV C, and TEV 1 compared to the controls when infected with TBRV.
Figure 7:
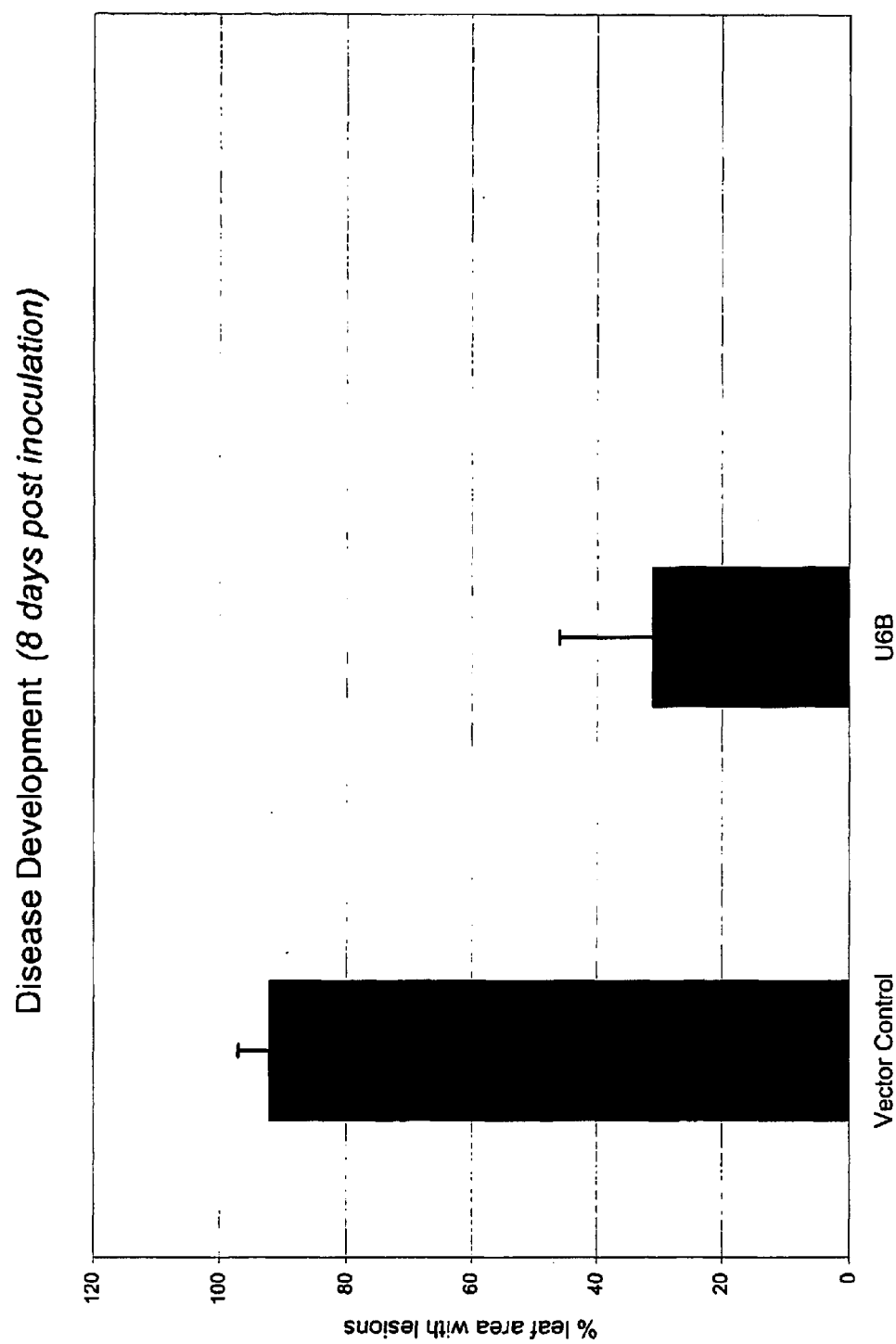
FIG. 7. Reduced fraction of leaf area giving rise to spores in transgenic line U-6B compared to the control when infected with blue mold.
Figure 8:
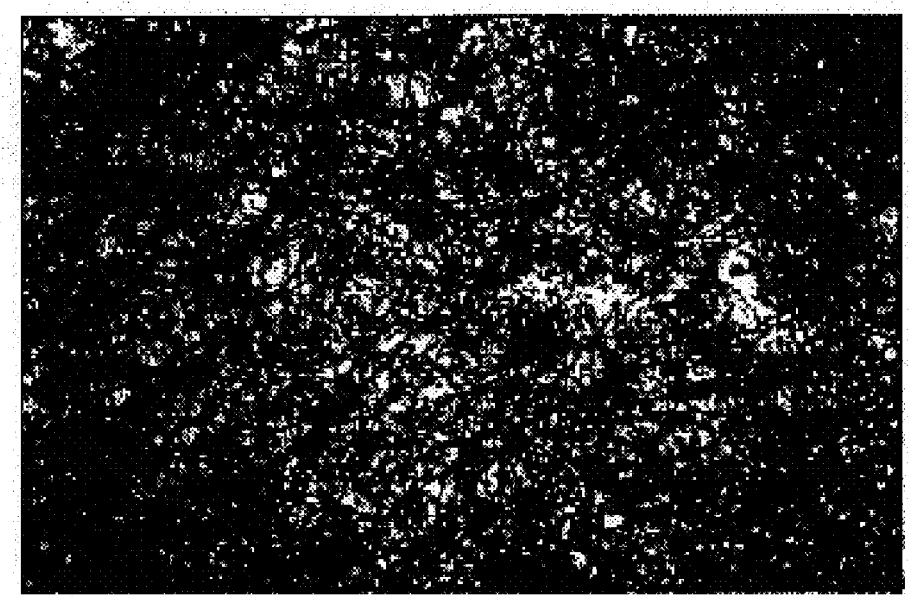
FIG. 8. Reduced growth of fungal hyphae in transgenic line U-6B compared to the control when infected with blue mold.
Figure 8:
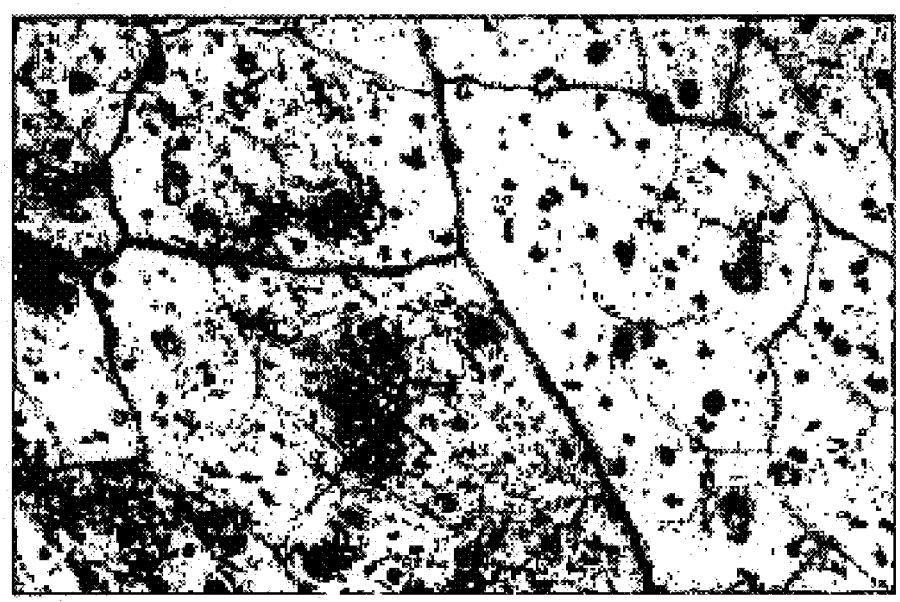
Figure 9:
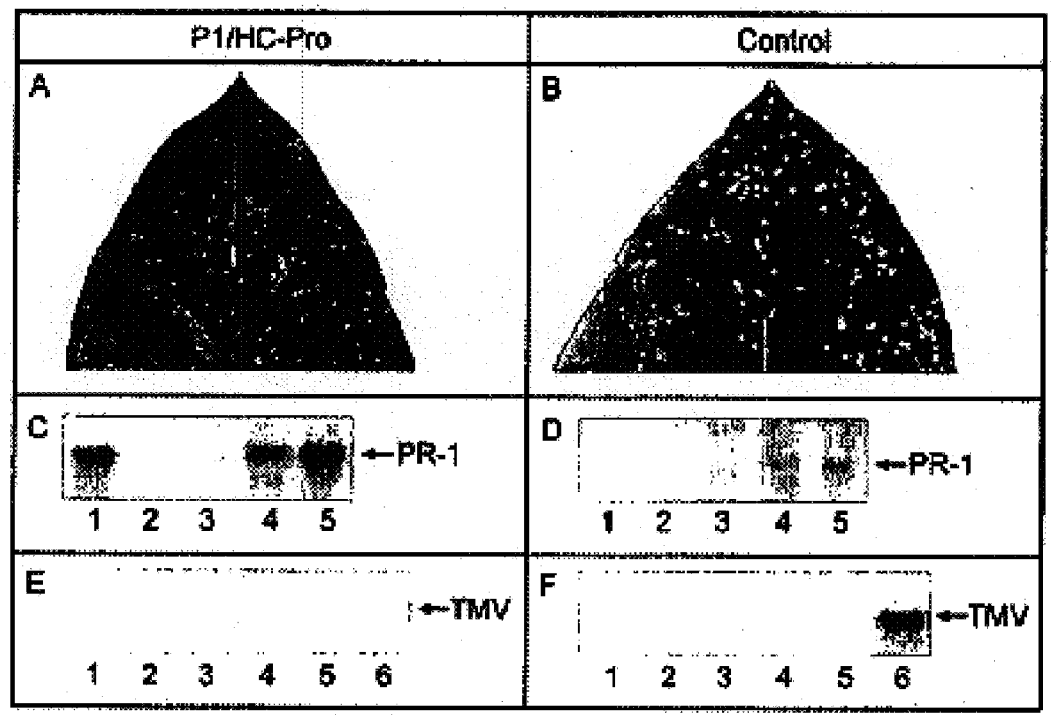
FIG. 9. TMV infection of P1/HC-Pro transgenic and control tobacco lines. (A, B) Sections of TMV-inoculated leaves showing reduced local lesion size on the P1/HC-Pro transgenic line (A) compared to the control line (B). (C, D) Time course of induction of PR-1 and (E, F) of accumulation of TMV RNA in TMV-inoculated leaves showing enhanced induction of PR-1 and reduced accumulation of TMV RNA in the P1/HC-Pro transgenic line (C, E) as compared to the control (D, F). Lanes 1–6 correspond to 0, 30, 38, 48, 60, and 102 hr post-inoculation, respectively. The leaf sections shown in (A, B) are from the leaves used for the 102 hr time point. For each time point, entire inoculated leaves were excised and ground up for RNA extraction.
Figure 10:
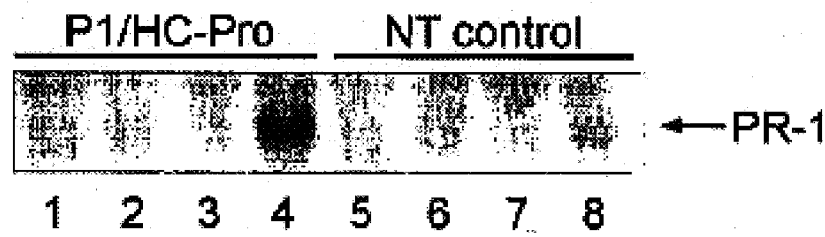
FIG. 10. Induction of PR-1 in P1/HC-Pro transgenic and control tobacco lines by different concentrations of INA, a synthetic inducer of SAR. RNA isolated from whole seedlings grown on media containing 0, 0.002, 0.01, and 0.1 mM INA (lanes 1–4 and 5–8, respectively) was probed for PR-1.

Results: all of the P1/HC-Pro transgenic lines carry the N gene, which confers gene-for-gene resistance to Tobacco Mosaic virus (TMV). The resistance is characterized by a localized hypersensitive response which results in necrotic lesions ("local" lesions) on the inoculated leaf and failure of the virus to spread systemically in the plant. That is, the virus remains restricted to the inoculated leaf. It is known that enhanced gene-for-gene resistance to TMV in *N. tabacum* strains carrying the N gene is induced by prior infection with the polyvirus PVY. The results of this experiment demonstrate that transgenic plants transformed with the potyviral P1/HC-Pro booster sequence exhibit much reduced levels of infection compared to control plants when infected with TMV (FIGS. 1, 2, and 3). In particular, the results of this experiment demonstrate that transgenic plants carrying the TEV wild type P1/HC-Pro booster sequence or the TEV 1 mutant P1/HC-Pro sequence exhibit enhanced resistance to TMV in the absence of prior infection with a potyvirus.

EXAMPLE 2

Enhanced Resistance to a Broad Range of Pathogens is Conferred by All Potyviral P1/HC-Pro Booster Sequences The ability to enhance resistance to pathogens is not a special property of TEV P1/HC-Pro, but a property of all potyviral P1/HC-Pro sequences. It is known that the potyvirus, PVY, induces resistance to TMV in *N. tabacum* Samsun carrying the N gene (Davis and Ross, *Virology* 34, 509–520, 1968). To demonstrate the equivalence of different potyviruses in inducing resistance to TMV, we repeated the experiment of Davis and Ross using TEV. Three each Xanthi and Vector tobacco plants were inoculated with TEV (Vector is Havana 425 transformed with vector and is the control line for the U6B line, transformed with the P1/HC-Pro booster sequence).

The results of this experiment showed that the Xanthi plants developed severe systemic symptoms of TEV infection. In contrast, the Vector plants developed only very mild, systemic symptoms. At 12 days post-inoculation, leaves showing symptoms of systemic TEV infection were inoculated with TMV. As a control, one plant each of Vector and Xanthi was initially mock-inoculated, and at the later time, inoculated with TMV on leaves corresponding to those on the TEV-infected plants. The secondary infection with TMV resulted in few, if any, local lesions on any of the leaves of Xanthi plants initially inoculated with TEV, while mock-inoculated controls exhibited numerous lesions. Additional results showed similar size local lesions on Vector plants that had been initially inoculated with TEV as on the mock-inoculated Vector plant.

Prior infection of Vector plants with TEV in this experiment had little effect on resistance to TMV probably because of the relatively poor systemic infection with TEV achieved. In the case of the Xanthi plants, however, a high level of systemic TEV infection was produced and the plants showed almost complete resistance to TMV.

EXAMPLE 3

Enhanced Resistance to Blue Mold Fungal Infection in *N Tabacum* Conferred by the Potyviral P1/HC-Pro Booster Sequences

*Peronsopora tabacina* Adam, obtained in Kentucky in 1979 and designated as isolate 79, was maintained by weekly transfers of sporangiospores on young cv. Ky 14 tobacco plants. Sporangiospores from sporulating leaves were washed off in distilled water, washed three times with distilled water, and collected on 3.0 micron membranes. Sporangiospores were then resuspended in distilled water and the concentration was adjusted, to $5\times10^4$ spores/ml. For challenge inoculations the plants (8 weeks old) were moved from the greenhouse, to a growth room illuminated with white flourescent light with a 14 h photoperiod at 23° C. and 70% relative humidity. The upper surfaces of leaves were sprayed with a uniform fine mist of inoculum. Plants were then covered with wet brown plastic bags and kept in the dark for 16 h. Typically 6–8 plants/line were inoculated in an individual experiment.

Resistance to *P. tabacina* was estimated 7 days after challenge by determining: (1) percentage of leaf area covered by lesions and (2) sporangiospore production per $cm^2$ of leaf area. After evaluation of percentage leaf area covered by lesions, the plants were sprayed with water on both sides of the leaves and kept in wet brown plastic bags for 16 h in the dark. Production of sporangiospores were assessed by cutting out sporulating leaf disks (3 $cm^2$), washing the spores off in distilled water, and counting them using a hemacytometer. Typically 6 replications were performed/line. Statistical analyses (Fisher's protected LSD) of data were performed using the StatPlus software package for MS Excel.

Trypan Blue Staining of *P. tabacina* Hyphae in plants:

*P. tabacina*-infected leaf discs (1 $cm^2$) were boiled in farmer's fluid (acetic acid:ethanol:chloroform at a 1:6:3 volume) until completely cleared. The discs were then incubated in a 0.03% trypan blue solution (w/v), consisting of trypan blue in a lactophenol/ethanol mixture (1:2 volume) at 60° C. for 4–6 h. The leaf discs were then destained in 2.5 g/ml chloral hydrate at room temperature until they were light blue. Discs were mounted in 50% glycerol and examined using a light microscope at 40× 100×, and 400× magnifications.

Results: Blue mold infection in P1/HC-Pro transgenic lines (U6B), as compared to control lines (Vector), shows the U6B plants have significantly milder symptoms than the Vector plants, as seen in the photograph in FIG. 5A. Additionally, U6B plants had lower spore counts than did the Vector controls, with a much smaller fraction of leaf area of U6B than of Vector giving rise to spores (See FIGS. 5B, 6, and 7). The photograph in FIG. 8 also demonstrates that U6B plants had less hyphal growth than did Vector controls.

EXAMPLE 4

Enhanced Resistance to Tomato Black Ring Virus (TBRV) Conferred by the Potyviral P1/HC-Pro Booster Sequences Infection with tomato black ring virus (TBRV), a nepovirus, was also examined in U6B plants and controls. A plant resistance gene for this virus, which causes systemic infection in tobacco, has not yet been identified. TBRV has a bipartite RNA genome, comprised of RNAs 1 and 2. Results of this experiment, comparing TBRV infection in inoculated leaves of P1/HC-Pro transgenic lines and control lines, showed less TBRV RNA in U6B plants than in Vector plants, as demonstrated by lanes 10–13 in the northern blot shown in FIG. 4.

Infection in transgenic lines containing mutant versions of the TEV P1/HC-Pro sequence was also examined. FIG. 4 shows northern blot results. As can be seen in lanes 1–9, less TBRV RNA was seen in lines TEV 1 and TEV C, which express mutant HC-Pro proteins that retain the ability to cause synergism and suppress silencing, than in line TEV K, which is silenced for an inactive mutant of HC-Pro. These lines all carry the TEV P1/HC-Pro sequence in the Xanthi background.

EXAMPLE 5

Booster Sequence Induced Resistance Enhanced SAR

The TMV-resistance of P1/HC-Pro-expressing tobacco plants (line U-6B) is shown by smaller lesions on inoculated leaves (FIG. 9, compare lesion size in panel 9A to that in panel 9B) associated with decreased levels of TMV (FIG. 9, compare the level of TMV RNA in panel E, lane 6 to that in panel F, lane 6). To determine if the enhanced resistance to TMV in the P1/HC-Pro-expressing plants involves SAR, we assayed the expression of PR-1 (a molecular marker for SAR) at various times after infection with TMV (FIGS. 9C and D). The P1/HC-Pro plants showed increased and earlier expression of PR-1 mRNA in response to TMV. A similar result was seen in blue mold infections (data not shown). These results show that the observed resistance to pathogens in P1/HC-Pro transgenic lines is due to an enhanced SAR response. In addition, about half of the uninfected P1/HC-Pro transgenic plants we have assayed are induced or PR-1 (FIG. 9C, lane 1 and data not shown), also indicating that expression of P1/HC-Pro potentiates the plant for induction of SAR.

Further evidence for the involvement of SAR in HC-Pro-induced resistance comes from experiments to determine the sensitivity of plants to 2,6-dichloroisonicotinic acid (INA), a salicylic acid (SA) analogue. SA is an intermediate in the SAR signaling pathway and is known to trigger expression of PR-1. FIG. 10 shows a northern blot of PR-1 induction in response to increasing levels of INA. PR-1 expression is more highly induced in the P1/HC-Pro-expressing transgenic line (FIG. 10, lanes 1–4) than in the control line (FIG. 10, lanes 5–8). This result indicates that the resistance of the P1/HC-Pro transgenic line due to an increased response to SA.

EXAMPLE 6

Transgenic Plants with Inducible Resistance

As will be apparent to those of ordinary skill in the art in view of the teachings set forth herein, in some circumstances it would be desirable to have plants in which the booster sequence induced resistance is an inducible characteristic. The plant of interest is engineered to contain the booster sequence under the control of an inducible promoter.

A number of inducible promoters are known in the art. For resistance genes, a pathogen-inducible promoter can be utilized. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245–254; Uknes et al. (1992) *Plant Cell* 4:645–656; and Van Loon (1985) *Plant Mol. Virol.* 4:111–116. Of particular interest are promoters that are expressed locally at or near the infection site. See, for example, Marineau et al. (1987) *Plant Mol. Biol.* 9:335–342; Matton et al. (1989) *Molecular Plant-Microbe Interactions* 2:325–331; Somsisch et al. (1986) *Proc. Natl. Acad Sci. USA* 83:2427–2430; Somsisch et al. (1988) *Mol. Gen. Genet.* 2:93–98; and Yang (1996) *Proc. Natl. Acad Sci. USA* 93:14972–14977. See also, Chen et al. (1996) *Plant J.* 10:955–966; Zhang et al. (1994) *Proc. Natl. Acad. Sci. USA* 91:2507–2511; Warner et al. (1993) *Plant J.* 3:191–201; Siebertz et al. (1989) *Plant Cell* 1:961–968; U.S. Pat. No. 5,750,386; Cordero et al. (1992) *Physiol. Mol. Plant Path.* 41:189–200; and the references cited therein.

Additionally, as pathogens find entry into plants through wounds or insect damage, a wound-inducible promoter may be used in the DNA constructs of the invention. Such wound-inducible promoters include potato proteinase inhibitor (pin 11) gene (Ryan (1990) *Ann. Rev. Phytopath.* 28:425–449; Duan et al. (1996) *Nature Biotechnology* 14:494–498; wun1 and wun2, U.S. Pat. No. 5,428,148; win1 and win2 (Stanford et al. (1989) *Mol. Gen. Genet.* 215:200–208); system in (McGurl et al. (1992) *Science* 225:1570–1573); WIP1 (Rohmeier et al. (1993) *Plant Mol. Biol.* 22:783–792; Eckelkamp et al. (1993) *FEBS Letters* 323:73–76); MP1 gene (Corderok et al. (1994) *Plant J.* 6(2):141–150; and the like. Such references are herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression; or a chemical-repressible promoter, where application of the chemical represses gene expression. Chemical-inducible promoters are known in the art and include, but are not limited to, the maize In2-2 promoter, which is activated by benzenesulfonamide herbicide safeners; the maize GST promoter, which is activated by hydrophobic electrophilic compounds that are used as pre-emergent herbicides; and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci USA* 88:10421–10425 and McNellis et al. (1998) *Plant J.* 14(2):247–257), and tetracycline-inducible and tetracycline-repressible promoters (see, for example, Gatz et al. (1991) *Mol. Gen. Genet.* 227:229–237, and U.S. Pat. Nos. 5,814,618 and 5,789,156), herein incorporated by reference.

Where enhanced expression in particular tissues is desired, tissue-specific promoters can be utilized. Tissue-specific promoters include those taught in Yamamoto et al. (1997) *Plant J.* 12(2)255–265; Kawamata et al. (1997) *Plant Cell Physiol.* 38(7):792–803; Hansen et al. (1997) *Mol. Gen Genet.* 254(3):337–343; Russel et al. (1997) *Transgenic Res.* 6(2):157–168; Rinehart et al. (1996) *Plant Physiol.* 112(3):1331–1341; Van Camp et al. (1996) *Plant Physiol.* 112(2):525–535; Canevasini et al. (1996) *Plant Physiol.* 112(2):513–524; Yamamoto et al. (1994) *Plant Cell Physiol.* 35(5):773–778; Lam (1994) *Results Probl. Cell Differ.* 20:181–196; Orozco et al. (1993) *Plant Mol. Biol.* 23(6):1129–1138; Matsuoka et al. (1993) *Proc Natl. Acad. Sci.* USA 90(20):9586–9590; and Guevara-Garcia et al. (1993) *Plant J.* 4(3):495–505.

Leaf-specific promoters can similarly be used if desired, and are taught in references which include Yamamoto et al. (1997) *Plant J.* 12(2):255–265; Kawamata et al. (1997) *Plant Cell Physiol.* 38(7):792–803; Hansen et al. (1997) *Mol. Gen. Genet.* 254(3):337–343; Russel et al. (1997) *Transgenic Res.* 6(2):157–168; Rinehart et al. (1996) *Plant Physiol.* 112(3):1331–1341; Van Camp et al. (1996) *Plant Physiol.* 112(2):525–535; Canevascini et al. (1996) *Plant Physiol.* 112(2):513–524; Yamamoto et al. (1994) *Plant Cell Physiol.* 35(5)773–778; Lam (1994) *Results Probl. Cell Differ.* 20:181–196; Orozco et al. (1993) *Plant Mol. Biol.* 23(6):1129–1138; Matsuoka et al. (1993) *Proc. Natl. Acad. Sci USA*:90(20) 9586–9590; and Guevara-Garcia et al. (1993) *Plant J.* 4(3):495–505.

Root-specific promoters are known and can be selected from the many available from the literature. See, for example, Hire et al. (1992) *Plant Mol. Biol.* 20(2):207–218 (soybean root-specific glutamine synthetase gene); Keller and Baumgartner (1991) *Plant Cell* 3(10):1051–1061 (root-specific control element in the GRP 1.8 gene of French bean); Sanger et al. (1990) *Plant Mol. Biol.* 14(3):433–443 (root-specific promoter of the mannopine synthase (MAS) gene of *Agrobacterium tumefaciens*) Miao et al. (1991) *Plant Cell* 3(1):11–22 (full-length cDNA clone encoding cytosolic glutamine synthetase (GS), which is expressed in roots and root nodules of soybean). Bogusz et al. (1990) *Plant Cell* 2(7):633–641 (root specific promoters from hemoglobin genes from the nitrogen-fixing nonlegume *Parasponia andersonii* and the related non-nitrogen-fixing nonlegume *Trema tomeniosa;* Leach and Aoyagi (1991) *Plant Science* (Limerick) 79(1):69–76 (rolC and rolD root-including genes of *Agrobacterium rhizogenes*); Teeri et al. (1989) *EMBO J.* 8(2):3431–350 (octopine synthase and TR2' gene); (VIENOD-GRP3 gene promoter); Kuster et al. (1995) *Plant Mol. Biol.* 29(4): 759–772 and Capana et al. (1994) *Plant Mol. Biol.* 25(4):681–691 (rolB promoter). See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *Bioassays* 10:108, herein incorporated by reference. Such seed-preferred promoters include, but are not limited to, Cim 1 (cytokinin-induced message); cZ10B1 (Maize 19 kDa zein); celA (cellulose synthase); gama-zein; Glob-1; bean β-phaseolin; napin; β-conglycinin; soybean lectin; cruciferin; maize 15 kDa zein; 22 kDa zein; 27 kDa zein; g-zein; waxy; shrunken 1; shrunken 2; globulin 1; etc.

The booster sequences of the invention may be provided in DNA constructs or expression cassettes for expression in the plant of interest. The cassette will include 5' and 3' regulatory sequences operably linked to a booster sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

The expression cassette may additionally contain at least one additional gene to be co-transformed into the organism. Alternatively, the additional gene(s) can be provided on multiple expression cassettes.

Such an expression cassette is provided with a plurality of restriction sites for insertion of the sequences of the invention to be under the transcriptional regulation of the regulatory regions. The expression cassette may additionally contain selectable marker genes.

The expression cassette will include in the 5'-3' direction of transcription, a transcriptional and translational initiation region, a DNA sequence of the invention, and a transcriptional and translational termination region functional in plants. The transcriptional initiation region, the promoter, may be native or homologous, or foreign or heterologous, to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcriptional initiation region that is heterologous to the coding sequence.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nucleic Acids Res.* 17:7891–7903; and Joshi et al. (1987) *Nucleic Acid Res.* 15:9627–9639.

Where appropriate, the gene(s) for which expression is desired may be optimized for expression in the transformed plant to enhance expression of the inserted gene(s). That is, the genes can be synthesized using plant-preferred codons corresponding to the plant of interest or by using codons that reflect the codon bias of the host plant than the native gene sequence. Methods are available in the art for synthesizing plant-preferred genes. See, for example, U.S. Pat. Nos. 5,380,831 and 5,436,391, and Murray et al. (1989) *Nucleic Acids Res.* 17:477–498, herein incorporated by reference.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region), Elroy-Stein et al. (1989) *PNAS USA* 86:6126–6130; potyvirus leaders, for example, TEV leader (Tobacco Etch Virus), Allison et al. (1986); MDMV Leader (Maize Dwarf Mosaic Virus), *Virology* 154:9–20; human immunoglobulin heavy-chain binding protein (BiP), Macejak et al. (1991) *Nature* 353:90–94; untranslated leader from the coat protein mRNA of alfalfa mosaic virus (AMV RNA 4), Jobling et al. (1987) *Nature* 325:622–625; tobacco mosaic virus leader (TMV), Gallie et al. (1989) in *Molecular Biology of RNA*, ed. Cech (Liss, N.Y.), pp. 237–256; and maize chlorotic mottle virus leader (MCMV), Lommel et al. (1991) *Virology* 81:382–385. See also, Della-Cioppa et al. (1987) *Plant Physiol.* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Plants transformed with a DNA construct of the invention may be produced by standard techniques known in the art for the genetic manipulation of plants. DNA can be transformed into plant cells using any suitable technology, such as a disarmed Ti-plasmid vector carried by Agrobacterium exploiting its natural gene transferability (EP-A-270355; EP-A-0116718; *NAR* 12(22):87211–87215 (1984); Townsend et al., U.S. Pat. No. 5,563,055); particle or microprojectile bombardment (U.S. Pat. No. 5,100,792; EP-A-444882; EP-A-434616; Sanford et al. U.S. Pat. No. 4,945,050; Tomes et al. (1995) *"Direct DNA Transfer Into Plant Cells via Microprojectile Bombardment,"* in *Plant Cell, Tissue, and Organ Culture: Fundamental Methods*, ed. Gamborg and Phillips (Springer-Verlag, Berlin); and McCabe et al. (1988) *Biotechnology* 6:923–926); microinjection (WO 92/09696; WO 94/00583; EP 331083; EP 175966; Green et al. (1987) *Plant Tissue and Cell Culture*, Academic Press; Crossway et al. (1986) *Biotechniques* 4:320–334); electroporation (EP 290395; WO 8706614; Riggs et al. (1986) *Proc. Nat. Acad. Sci. USA* 83:5602–5606; D'Halluin (1992) *Plant Cell* 4:1495–1505); other forms of direct DNA uptake (DE 4005152; WO 9012096; U.S. Pat. No. 4,684,611; Paszkowski et al. (1984) *EMBO J.* 3:2717–2722); liposome-mediated DNA uptake (e.g., Freeman et al. (1984) *Plant Cell Physiol.* 29:1353); or the vortexing method (e.g., Kindle (1990) *Proc. Nat. Acad. Sci USA* 87:1228). Physical methods for the transformation of plant cells are reviewed in Oard (1991) *Biotech. Adv.* 9:1–11. See generally, Weissinger et al. (1988) *Ann. Rev. Genet.* 22:421–477; Sanford et al. (1987) *Particulate Science and Technology* 5:27–37; Christou et al. (1988) *Plant Physiol.* 87:671–674; McCabe et al. (1988) *Bio/Technology* 6:923–926; Finer and McMullen (1991) *In Vitro Cell Dev. Biol.* 27P:175–182; Singh et al. (1998) *Theor. Appl. Genet.* 96:319324; Datta et al. (1990) *Biotechnology* 8:736–740; Klein et al. (1988) *Pro. Natl. Acad. Sci. USA* 85:4305–4309; Klein et al. (1988) *Biotechnology* 6:559–563; Tomes, U.S. Pat. No. 5,240,855; Buising et al., U.S. Pat. Nos. 5,322,783 and 5,324,646; Klein et al. (1988) *Plant Physiol.* 91:440–444; Fromm et al. (1990) *Biotechnology* 8:833–839; Hooykaas-Van Slogteren et al. (1984) *Nature* (London) 311:763–764; Bytebier et al. (1987) *Proc. Natl. Acad. Sci. USA* 84:5345–5349; De Wet et al. (1985) in *The Experimental Manipulation of Ovule Tissues*, ed. Chapman et al. (Longman, N.Y.), pp. 197–209; Kaeppler et al. (1990) *Plant Cell Reports* 9:415–418 and Kaeppler et al. (1992) *Theor. Appl. Genet.* 84:560–566; Li et al. (1993) *Plant Cell Reports* 12:250–255; Christou and Ford (1995) *Annals of Botany* 75:407–413; and Osjoda et al. (1996) *Nature Biotechnology* 14:745–750; all of which are herein incorporated by reference.

Agrobacterium transformation is widely used by those skilled in the art to transform dicotyledonous species.

Recently, there has been substantial progress towards the routine production of stable, fertile transgenic plants in almost all economically relevant monocot plants (Toriyama et al. (1988) Bio/Technology 6:1072–1074; Zhang, et al. (1988) Plant Cell Rep. 7:379–384; Zhang et al. (1988) Theor. Appl. Genet. 76:835–840; Shimamoto et al. (1989) Nature 338:274–276; Datta et al. (1990) Bio/Techology 8:736–740; Christou et al. (1991) Biotechnology 9:957–962; Peng et al. (1991) International Rice Research Institute, Manila, Philippines, pp. 563–574; Cao et al. (1992) Plant Cell Rep. 11:585–591; Li et al. (1993) Plant Cell Rep. 12:250–255; Rathore et al. (1993) Plant Mol. Biol. 21:871–884; Fromm et al. (1990) Bio/Technology 8:833–839; Gordon-Kamm et al. (1990) Plant Cell 2:603–618; D'Halluin et al. (1992) Plant Cell 4:1495–1505; Walters et al. (1992) Plant Mol. Biol. 18:189–200; Koziel et al. (1993) Bio/technology 11:194–200; Vasil, I. K. (1994) Plant Mol. Biol. 25:925–937; Weeks et al. (1993) Plant Physiol. 102:1077–1084; Somers et al. (1992) Bio/Technology 10:1589–1594; WO 92/14828). In particular, Agrobacterium mediated transformation is now emerging also as a highly efficient transformation method in monocots (Hiei, et al. (1994) The Plant Journal 6:271–282). See also, Shimamoto, K. (1994) Current Opinion in Biotechnology 5:158–162; Vasil, et al. (1992) Bio/Technology 10:667–674; Vain, et al. (1995) Biotechnology Advances 13(4):653–671; Vasil et al. (1996) Nature Biotechnology 14:702.

Microprojecile bombardment, electroporation, and direct DNA uptake are preferred where Agrobacterium is inefficient or ineffective. Alternatively, a combination of different techniques may be employed to enhance the efficiency of the transformation process, e.g., bombardment with Agrobacterium-coated microparticles (EP-A-486234) or microprojectile bombardment to induce wounding followed by co-cultivation with Agrobacterium (EP-A-486233).

Following transformation, a plant may be regenerated, e.g., from single cells, callus tissue or leaf discs, as is standard in the art. Almost any plant can be entirely regenerated from cells, tissues, and organs of the plant. Available techniques are reviewed in Vasil et al. (1984) in Cell Culture and Somatic Cell Genetics of Plants, Vols. I, II, and III, Laboratory Procedures and Their Applications (Academic press); and Weissbach et al. (1989) Methods for Plant Mol. Biol.

The transformed plants may then be grown, and either pollinated with the same transformed strain or different strains, and the resulting line having expression of the desired phenotypic characteristic identified. Two or more generations may be grown to ensure that expression of the desired phenotypic characteristic is stably maintained and inherited, and then seeds harvested to ensure expression of the desired phenotypic characteristic has been achieved.

The particular choice of a transformation technology will be determined by its efficiency to transform certain plant species as well as the experience and preference of the person practicing the invention with a particular methodology of choice. It will be apparent to the skilled person that the particular choice of a transformation system to introduce nucleic acid into plant cells is not essential to or a limitation of the invention, nor is the choice of technique for plant regeneration.

Also according to the invention, there is provided a plant cell having the constructs of the invention. A further aspect of the present invention provides a method of making such a plant cell involving introduction of a vector including the construct into a plant cell. For integration of the construct into the plant genome, such introduction will be followed by recombination between the vector and the plant cell genome to introduce the sequence of nucleotides into the genome. RNA encoded by the introduced nucleic acid construct may then be transcribed in the cell and descendants thereof, including cells in plants regenerated from transformed material. A gene stably incorporated into the genome of a plant is passed from generation to generation to descendants of the plant, so such descendants should show the desired phenotype.

The present invention also provides a plant comprising a plant cell as disclosed. Transformed seeds and plant parts are also encompassed.

In addition to a plant, the present invention provides any clone of such a plant, seed, selfed or hybrid descendants, and any part of any of these, such as cuttings or seed. The invention provides any plant propagule, that is any part which may be used in reproduction or propagation, sexual or asexual, including cuttings, seed, and so on. Also encompassed by the invention is a plant which is a sexually or asexually propagated off-spring, clone, or descendant of such a plant; or any part or propagule of said plant, offspring, clone, or descendant. Plant extracts and derivatives are also provided.

The present invention may be used for transformation of any plant species, including, but not limited to, corn (Zea mays), canola (Brassica napus, Brassica rapa ssp.), alfalfa (Medicago sativa), rice (Oryza sativa), rye (Secale cereale), sorghum (Sorghum bicolor, Sorghum vulgare), sunflower (Helianthus annuus), wheat (Triticum aestivum), soybean (Glycine max), tobacco (Nicotiana tabacum), potato (Solanum tuberosum), peanuts (Arachis hypogaea), cotton (Gossypium hirsutum), sweet potato (Ipomoea batatus), cassava (Manihot esculenta), coffee (Cofea ssp.), coconut (Cocos nucifera), pineapple (Ananas comosus), citrus trees (Citrus spp.), cocoa (Theobroma cacao), tea (Camellia sinensis), banana (Musa spp.), avocado (Persea americana), fig (Ficus casica), guava (Psidium guajava), mango (Mangifera indica), olive (Olea europaea), papaya (Carica papaya), cashew (Anacardium occidental), macadamia (Macadamia integrifolia), almond (Prunus amygdalus), sugar beets (Beta vulgaris), oats, barley, vegetables, ornamentals, and conifers.

Preferably, plants of the present invention are crop plants (for example, cereals and pulses, maize, wheat, potatoes, tapioca, rice, sorghum, millet, cassava, barley, pea, and other root, tuber, or seed crops. Important seed crops are oil-seed rape, sugar beet, maize, sunflower, soybean, and sorghum. Horticultural plants to which the present invention may be applied may include lettuce; endive; and vegetable brassicas including cabbage, broccoli, and cauliflower; and carnations and geraniums. The present invention may be applied to tobacco, cucurbits, carrot, strawberry, sunflower, tomato, pepper, chrysanthemum, poplar, eucalyptus, and pine.

Grain plants that provide seeds of interest include oil-seed plants and leguminous plants. Seeds of interest include grain seeds, such as corn, wheat, barley, rice, sorghum, rye, etc. Oil seed plants include canola, cotton, soybean, safflower, sunflower, Brassica, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or scope of the present invention. In addition, it should be understood that aspects of the various embodiments may be interchanged both in whole or in part.

It should be understood that the examples and embodiments described herein are for illustrative purposes only and that various modifications or changes in light thereof will be suggested to persons skilled in the art and are to be included within the spirit and purview of this application and the scope of the appended claims. All patents, patent applications, provisional applications, and publications referred to or cited herein, or for which a claim for benefit of priority has been made, are incorporated by reference in their entirety to the extent they are not inconsistent with the explicit teachings of this specification.

What is claimed is:

1. A method of protecting tobacco plants from pathogens which comprises:
   a) transforming a tobacco plant cell with a functional gene that suppresses post transcriptional gene silencing (PTGS), said functional gene comprising a potyvirus P1/HC-Pro sequence operably linked to an inducible promoter,
   b) regenerating a transformed plant from said transformed cell; and
   c) selecting a transformed plant having enhanced resistance to at least one pathogen that elicits the systemic acquired resistance response.

2. The method according to claim 1, wherein said method further comprises collecting seeds from said plant.

3. The method according to claim 2, further comprising the step of using the seeds of said plant to breed new plant lines that are protected from pathogens by expression of said P1/HC-Pro sequence.

4. The method according to claim 3, further comprising the step of collecting seed from said plant lines.

5. The method according to claim 1, further comprising the steps of:
   a) collecting seeds of the plant, and
   b) using the seeds to breed new plant lines that are protected from pathogens by expression of the functional gene that suppresses PTGS.

6. The method according to claim 5, further comprising the step of collecting seed from said plant lines.

7. The method according to claim 1, wherein said P1/HC-Pro sequence comprises the 5' proximal region of the tabacco etch virus (TEV) genome.

8. The method according to claim 1, wherein said inducible promoter is pathogen-inducible promoter.

9. The method according to claim 1, wherein said inducible promoter is a wound-inducible promoter.

10. The method according to claim 1, wherein said transformed plant comprises the N gene.

11. The method according to claim 1, wherein said pathogen is selected from the group consisting of tobacco mosaic virus, *Peronospora tabacina,* and tomato black ring virus.

12. The method according to claim 10, wherein said pathogen is selected from the group consisting of tobacco mosaic virus, *Peronospara tabaccina,* and tomato black ring virus.

* * * * *